United States Patent [19]

Halliday

[11] Patent Number: 5,471,995

[45] Date of Patent: Dec. 5, 1995

[54] SPINE CONTOUR GAUGE AND METHOD

[76] Inventor: Michael V. Halliday, 140 E. 300 South, Salem, Utah 84653

[21] Appl. No.: 162,598

[22] Filed: Dec. 3, 1993

[51] Int. Cl.$^6$ .................................................. G01B 5/00
[52] U.S. Cl. .......................... 128/781; 128/774; 33/514.2
[58] Field of Search .................................... 128/774, 781, 128/782; 33/511, 512, 519.2, 515

[56] References Cited

U.S. PATENT DOCUMENTS

| | | | |
|---|---|---|---|
| 874,091 | 12/1907 | Lemcke. | |
| 1,012,372 | 12/1911 | Landenberger. | |
| 1,234,527 | 7/1917 | Berriman. | |
| 2,295,447 | 9/1942 | Bierman | 33/175 |
| 2,378,039 | 6/1945 | Schenker | 73/172 |
| 2,523,647 | 9/1950 | Burk | 33/175 |
| 4,425,713 | 1/1984 | Rotella | 33/515 |
| 4,444,204 | 4/1984 | Bryant et al. | 128/781 |

OTHER PUBLICATIONS

Pearsall et al., "Comparison of Three Noninvasive Methods for Measuring Scoliosis", *Physical Therapy*, vol. 72, No. 9, pp. 648–657, (Sep. 1992).
Product Brochure of Saunders Therapy Products, "STP Electronic Inclinometer", (1991).
Product Brochure of Cybex Extremity Systems, (1991).
Correspondence and Product Brochure of SR Associates, "SR360 Flexometer and Portable Master's Spinalyzer", (1989).
Product Brochure of Faro Medical Technologies, Inc., "Axis Muscle Tester", (1989).
Product Brochure of Faro Medical Technologies, Inc., "2D–Xray Analyzer", (1989).
Bennett et al., "Comparison of Integrated Electromyographic Activity and Lumbar Curvature During Standing and During Sitting in Three Chairs", *Physical Therapy*, vol. 69, No. 11, pp. 902–913, (Nov. 1989).
Nosse et al., "Spinal Effects of Head–down Tilting", *Physical Therapy*, vol. 68, No. 1, pp. 60–66, (Jan. 1988).
Fulton, "Lower Back Pain: New Protocols for Diagnosis and Treatment", Rehab Management, (Nov./Dec. 1988).
Nosse, "Measurement System for Low Back Contour", *Physical Therapy*, vol. 65, No. 8, pp. 212–213, (Aug. 1985).
Product Brochure of Chattanooga Group, Inc., "The Chattecx Lumbar Motion Monitor", (date unknown).
Correspondence and Product Advertisement of Spinex Medical Technologies, Inc., "The Spinoscope, Technology for the Objective Assessment of Spinal Capacity", (date unknown).
Product Brochure of OSI Orthopedic Systems, Inc., "The CA–6000 Spine Motion Analyzer", (date unknown).
Product Brochure of Motion Analysis Corporation, "SpineTrak", (date unknown).
Declaration of Michael V. Halliday, (Feb. 16, 1994).
Photograph of "SpG4000 Spinal Goniograph".
Post card of Spinal Goniograph by Michael V. Halliday, 1992.

*Primary Examiner*—Sam Rimell
*Attorney, Agent, or Firm*—Madson & Metcalf

[57] ABSTRACT

A device and methods for quantitatively measuring spinal contours and flexibility are provided. The device includes a plurality of substantially parallel coplanar shafts slidable within a guide block. One end of each shaft lies within a chamber which may be pressurized, thereby urging the opposite ends of the shafts to gently deploy against a patient's spine. The shafts may be locked in position with a keeper strip. The relative positions of the shafts may be quantified, and these quantified positions may be processed according to methods of the present invention to obtain reliable quantitative summaries of the curvature and flexibility of selected spinal contours.

36 Claims, 4 Drawing Sheets

SPINE CONTOUR GAUGE AND METHOD

FIELD OF THE INVENTION

The present invention relates to a device and method for quantitatively measuring spinal contours and spinal flexibility. More particularly, the invention relates to a device having a plurality of shafts configured to deploy against a patient's spine in response to gas pressure, and to methods for measuring the flexibility of chosen spinal segments and for measuring changes in posture by utilizing multiple readings obtained with the device.

TECHNICAL BACKGROUND OF THE INVENTION

Back injuries are an expensive, frustrating, and widespread problem. People who suffer from back problems include those with bad posture, trauma victims, recovering spinal surgery patients, elderly persons undergoing osteoporosis and the posture changes attendant with aging, and expectant mothers. Such people seek held from a variety of medical professionals, including clinical physicians and physical therapists. In response, these medical professionals diagnose back problems, recommend exercise regimens and other treatments, and monitor each patient's progress toward recovery or proper spinal posture and flexibility.

In order to properly diagnose, treat, and monitor spinal problems, however, medical professionals need accurate information. Two types of information are desirable. First, professionals need accurate measurements which capture the spinal shape or contour. Second, they need accurate measurements of the flexibility of a chosen spinal segment. Both the contour and the flexibility measurements must be obtained in a reliable and repeatable manner from direct examination of the patient.

When a healthy human spine is viewed laterally, it presents several curves corresponding to different regions of the spinal column. These are called the cervical, dorsal, lumbar, and pelvic curves. Accurate measurements of these curves assists medical professionals in diagnosing and monitoring back problems. The relative size of two curves, for instance, may be an important diagnostic indicator. Similarly, reliable information about the changes in a given curve over time can be an important tool in monitoring the patient's progress. It may also be useful to measure the spine with the patient in various positions, including standing straight, sitting, lying, bending forward to flex the spine, and bending backward to extend the spine.

Several attempts have been made to reliably quantify spinal contours and flexibility. For instance, images of the spine may be reliably captured using conventional X-ray equipment, magnetic nuclear resonance devices, and known tomography tools. However, such devices are often prohibitively large and expensive for an individual medical professional to obtain. Each use of such a device may also be quite costly. Moreover, these devices are rarely portable, and they require additional specialists as operators.

Another drawback of tomography tools and similar devices is that they do not address the issue of how to reduce the vast amount of data produced to a form usable by medical professionals and understandable by their patients. Because treatment of back problems often involves exercise regimens and posture modification which can only be carried out by the patient, it is particularly important that measurements be presented in a form that can be explained to patients and used to motivate them. The fact that interpretation of tomographic images typically requires specialized professional training is thus a severe disadvantage.

Goniometers and inclinometers have also been tested as tools for measuring the spine. Although such devices are portable and relatively easy to use, the information they provide is insufficient. Even if utilized in pairs, these devices can only measure angles. As noted above, however, professionals need accurate measurements of spinal curves. Angular measurements are appropriate when examining joints such as the knee or the elbow, but they have very limited utility in connection with the spine.

Lacking adequate tools, medical professionals often rely on simple visual inspection of their patients' spines. This approach has the advantage of being relatively inexpensive, portable, versatile, and easy to use. Unfortunately, however, "eyeballing" the spinal curves produces unreliable results. The measurements are subjective, not quantitative and reproducible. The absence of repeatable quantitative spine measurements is particularly troublesome when attempts are made to monitor the patient's progress over time. Moreover, such visual inspections produce no visible record that can be presented to the patient for purposes of explanation and motivation.

Thus, it would be an advancement in the art to provide a gauge for reliably measuring spinal contours.

It would also be an advancement to provide such a gauge which can be operated by a medical professional with little additional training.

It would be a further advancement in the art to provide a spinal contour gauge which is inexpensive to operate, portable, and relatively small.

It would be an additional advancement in the art to provide methods for using such a gauge to produce spinal measurements in a form that is useful to medical professionals and understandable by their patients.

It would also be an advancement to provide methods for using such a gauge to reliably quantify the flexibility of selected spinal segments.

Such a spinal contour gauge and related methods are disclosed and claimed herein.

BRIEF SUMMARY OF THE INVENTION

The present invention provides a spinal contour gauge and related methods for use in diagnosing, treating, and monitoring back problems. In a present embodiment, the gauge includes a plurality of parallel coplanar shafts disposed in bores in a guide block. The guide block, and a frame which is secured to the guide block, substantially define a chamber that is in fluid communication with a pressurized gas source. The device also includes a gas outlet for releasing pressurized gas from the chamber.

The shafts are disposed with one end within the chamber and the other end extending outside the chamber. The external end of each shaft is covered with a soft material such as latex or rubber. The internal end of each shaft has a stop to prevent the shaft from passing through the bore and exiting the chamber. The body of each shaft is preferably made of aluminum.

The guide block bores in which the shafts are positioned are made of a synthetic resin. The body of each shaft fits snugly within its corresponding bore in the guide block to reduce the loss of gas from within the chamber through the bores. However, the coefficient of friction between the bores and the shafts is small enough to permit shaft deployment in response to very low chamber gas pressures.

One side of the chamber is formed of a transparent material such as plastic or acrylic, so that the internal ends of the shafts are visible outside the chamber. Measuring indicia for indicating the position of the internal ends are located on the transparent chamber side. Identifying indicia identifying the individual shafts are located along one edge of the chamber. Thus, the position of each shaft relative to the guide block may be quantified as a pair of coordinates.

The present embodiment also includes a keeper strip for locking the deployed shafts into position. The keeper strip is a rigid strip with diagonal slots slidably mounted to the guide block by pins through the slots. The keeper strip is movable from a released position in which it does not engage the shafts to a locked position in which the keeper strip presses each shaft against an interior edge of the bore through which the shaft passes, thereby locking the shafts in position relative to the guide block.

In addition, the present embodiment includes a limiter slide for preventing selected shafts at one end of the chamber frame from fully deploying. The limiter slide includes a bracket and a bar. The bracket is mounted near the guide block. The bar is configured for slidable engagement relative to the bracket from a position in which the bar does not engage any shaft to at least one position in which the bar engages the external end of at least one shaft, thereby preventing movement of the engaged shaft relative to the guide block beyond the bar.

The chamber frame may be mounted on a mobile stand having a positionable arm, thereby permitting easy deployment of the shafts against the backs of patients who are in various positions. Alternatively, the chamber frame may be mounted on a vertical wall mount and may be stored against the wall in a space less than about five centimeters deep.

In operation, a patient is first placed in a clinically useful position, such as standing or lying, with the patient's spine either flexed, at rest, or in extension. Next, the spine contour gauge is positioned near the patient's spine. The shafts may then be deployed by permitting pressurized gas to flow into the chamber. The increased gas pressure within the chamber gently urges the shafts to slide out of the chamber, thereby deploying the external ends of the shafts against the tissue near the patient's spine. The shaft velocity is low, and the external ends of the shafts are covered with a soft material, so the deployment does not discomfort the patient. After the shafts are deployed, the keeper strip is urged into its locking position to preserve the shaft positions, and the gas outlet is opened to release the pressure within the chamber.

By reading the measuring indicia and the identifying indicia, the medical professional then obtains quantified shaft positions which correspond to the contours of the patient's spine. These quantified shaft positions may be processed in various ways to obtain a quantitative summary that is useful to the professional and understandable by the patient. For instance, the quantitative summaries may be used diagnostically to compare two curves, such as the lumbar and dorsal curves. Quantitative summaries may also be used to compare the same curve with itself at different times, thereby providing a reliable, quantitative measure of the patient's progress. Moreover, quantitative summaries of a selected spinal contour obtained from different patient positions during one examination may be used to reliably quantify the flexibility of that contour.

These and other features and advantages of the present invention will become more fully apparent through the following description and appended claims taken in conjunction with the accompanying drawings.

BRIEF DESCRIPTION OF THE DRAWINGS

In order that the manner in which the above-recited and other advantages and features of the invention are obtained, a more particular description of the invention summarized above will be rendered by reference to the appended drawings. Understanding that these drawings only provide selected embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
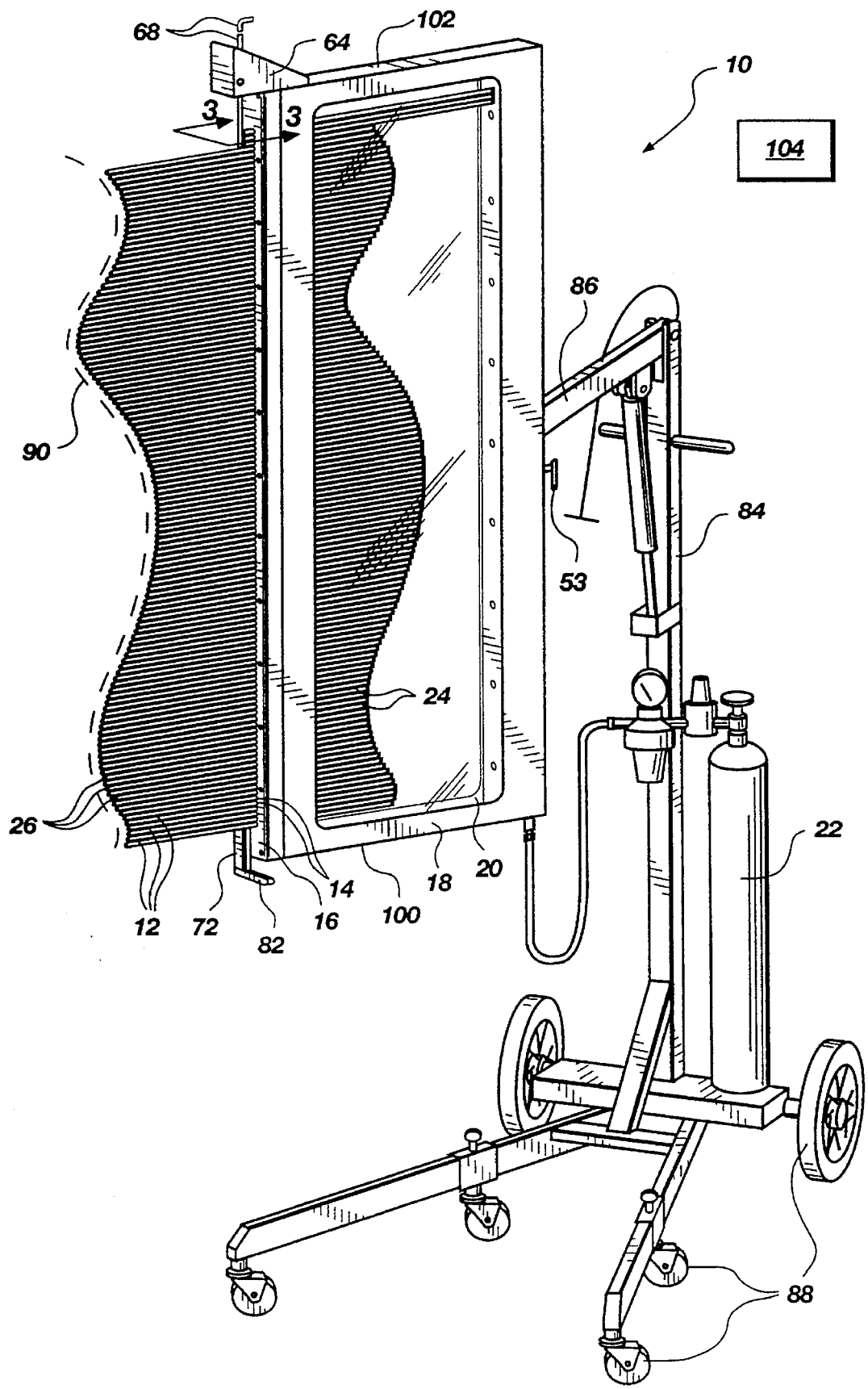
FIG. 1 is a perspective view of an embodiment of the device of the present invention, illustrating a chamber frame secured to a positionable arm mounted on a mobile stand.

Reference is now made to the figures wherein like parts are referred to by like numerals. The present invention relates to a spinal contour gauge and to methods for quantitatively measuring spinal contours and spinal flexibility. An embodiment of the spinal contour gauge is generally designated at 10 in FIG. 1.

The gauge 10 includes a plurality of parallel coplanar shafts 12 disposed in bores 14 in a guide block 16. The guide block 16 and a frame 18 secured to the guide block 16 substantially define a chamber 20 that is in fluid communication with a pressurized gas source 22.

The chamber 20 contains an internal end 24 of each shaft 12, while the external end 26 of each shaft 12 lies outside the chamber 20. As shown best in FIG. 2, the external end 26 of each shaft 12 is covered with a tip 28 of soft material such as latex or rubber. The internal end 24 of each shaft 12 has a stop 30 with a maximum diameter sufficiently larger than the diameter of the bore 14 to prevent the shaft 30 from passing through the bore 14 and exiting the chamber 20.

A portion of each shaft 12 between the ends 24 and 26 constitutes the body 32 of the shaft 12. The body 32 of each shaft 12 is preferably made of aluminum. The body 32 is polished or otherwise provided with a smooth finish. The body 32 may be solid or hollow, but in the latter case, the end 24 of the shaft 12 should be plugged so that pressurized gas from the gas source (22 in FIG. 1) does not leak out of the chamber 20 through the hollow interior of the shaft 12.

The frame 18 may be formed of plastic, aluminum, or other materials which are rigid and relatively light in weight. The frame is capable of holding the guide block 16 and the sides 36 and 38 in place such that the chamber 20 will hold pressures sufficient to overcome the friction between the shafts 12 and the guide block 16, as described below.

The guide block 16 in which the shafts 12 are positioned is preferably made of a synthetic resin such as that sold under the mark DELRIN by E. I. Du Pont de Nemours and Co., or that sold under the mark ERTALYTE by Erta, N. V., of Belgium. Appropriate synthetic resins have several important characteristics. For instance, an appropriate resin does not react with the gas used to pressurize the chamber. Thus, the resin does not corrode, change size, produce films or other undesirable by-products, or react in other ways that interfere with the hygienic and efficient operation of the device 10.

Appropriate resins also have a sufficiently low coefficient of friction when engaging the shafts 12 to permit deployment of the shafts under relatively low pressures in the chamber 20. A resin is not appropriate if the coefficient of friction requires about seven kilopascals or higher pressures within the chamber 20 to urge the shafts 12 outward. In a preferred embodiment, the materials for constructing the guide block 16 and the shafts 12 are selected such that the shafts 12 will deploy in response to an actuating pressure of about 5 to 50 kilopascals in the chamber 20, and preferably of about 5 to 10 kilopascals.

Finally, appropriate resins are structurally stable. The guide block 16 is a structural member of the device 10. As described herein, various components such a keeper strip and chamber sides are secured to the guide block 16, so the resin comprising the guide block 16 must be sufficiently rigid to support these components and to withstand forces created by pressurizing the chamber 20.

The bores 14 in the guide block 16 which guide the shafts 12 are spaced closely enough to obtain an accurate measurement of the selected contours when the shafts 12 are deployed against the patient's spine. A preferred embodiment includes about ninety shafts 12 per meter of length of the guide block 16. However, it will be appreciated by those of skill in the art that more or fewer shafts per meter may also be utilized according to the teachings of the present invention.

Figure 3:
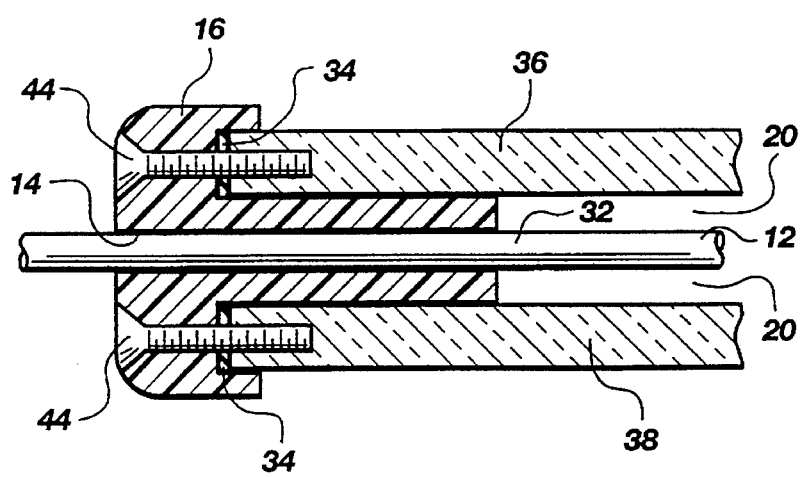
FIG. 3 is a partial cross-sectional view, taken along line 3—3 of FIG. 1, further illustrating the guide block, bore, shaft, and sides of the chamber frame.

As shown best in FIG. 3, the body 32 of each shaft 12 fits snugly within its corresponding bore 14 in the guide block 16. In the embodiment shown, the diameter of the shaft 32 is 5575.3 plus or minus 10.16 micrometers (0.2195 plus or minus 0.0004 inches). The bore 14 is formed with a reamer having a stated diameter of 5613.4 micrometers (0.2210 inches). After being initially reamed, the DELRIN about the bore 14 collapses inward slightly, so the bore 14 assumes an inner diameter of 5588.0 plus or minus 12.70 micrometers (0.2200 plus or minus 0.0005 inches).

The fit of the shaft 12 within the bore 14 reduces the loss of pressurized gas from within the chamber 20 through the bores 14. However, in spite of the snug fit between shafts 12 and the guide block 16, the coefficient of friction between the DELRIN bores 14 and the aluminum shafts 12 described herein is small. The shafts 12 will slide through the bores 14 in response to pressures within the chamber 20 as low as about seven kilopascals (about one pound per square inch) above atmospheric pressure.

Figure 2:
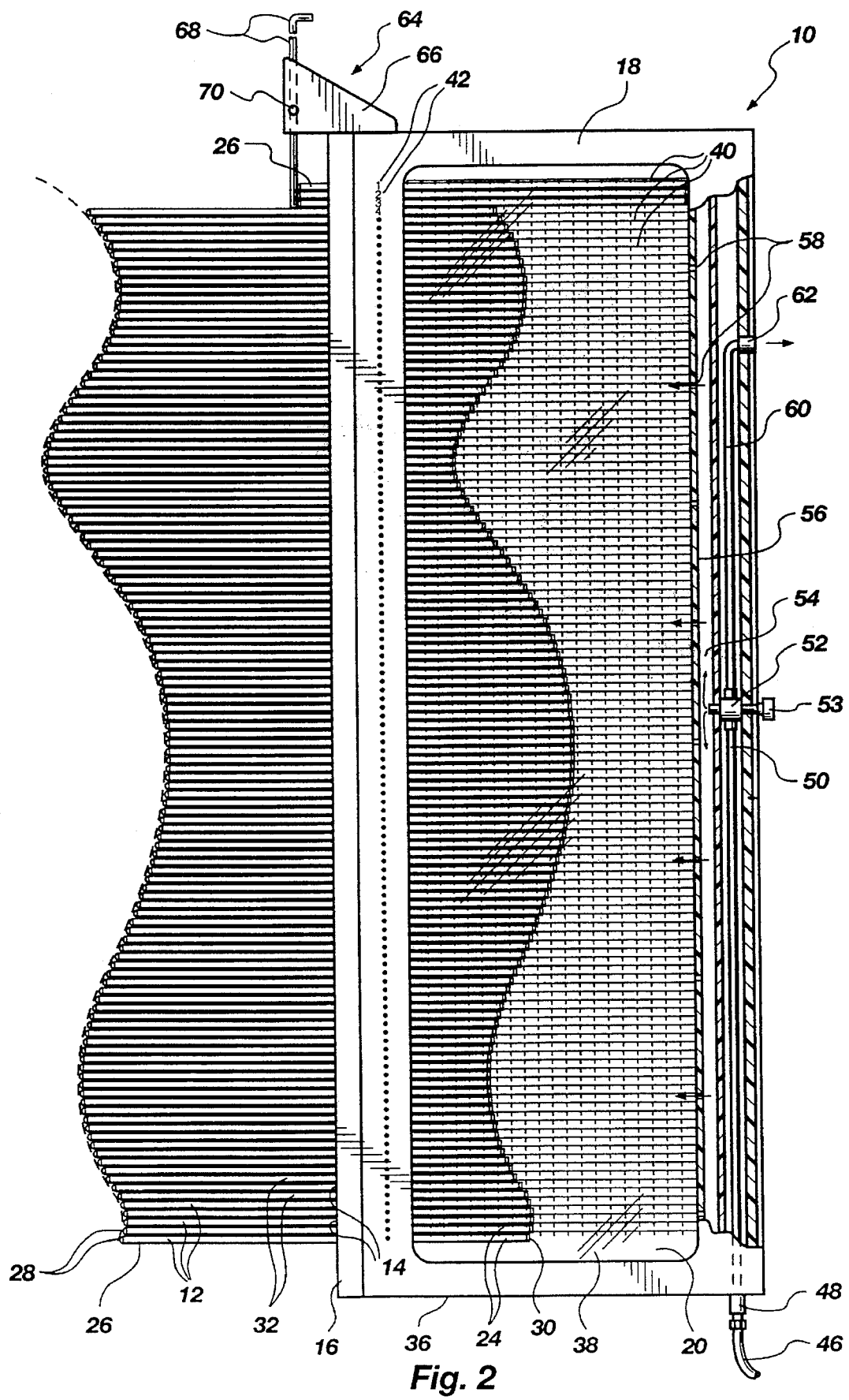
FIG. 2 is an enlarged partial cut-away view of the chamber frame shown in FIG. 1, illustrating paths pressurized gas may take into and out of the chamber.

As shown in FIG. 3, the chamber 20 is bordered by two sides 36 and 38. The front side 38 is formed of a transparent material such as plastic or acrylic. One acceptable material is a plastic sheet sold under the mark LUCITE by E. I. Du Pont de Nemours and Co. The front side 38 is preferably scratch-resistant. Because the front side 38 is transparent, the internal ends 24 of the shafts 12 are visible outside the chamber 20, as illustrated in FIG. 2. The rear side 36 of the chamber 20 is colored an opaque blue to make viewing the ends 24 easier.

Measuring indicia 40 for indicating the position of the internal ends 40 are located on the transparent chamber side 38. Alternatively, the indicia 40 may be placed on the opaque side 36 if the transparent side 38 is sufficiently scratch-resistant and does not otherwise render it difficult to read indicia 40 placed on the opaque side 36. The measuring indicia 40 may include numbers as well as measuring lines, as on a conventional ruler. Identifying indicia 42 identifying the individual shafts 12 are located along one edge of the chamber 20. Thus, the position of each shaft 12 relative to the guide block 16 may be quantified as a pair of coordinates, wherein one coordinate identifies the shaft 12 and the other coordinate specifies the distance of the end 24 of the shaft 12 from the guide block 16 measured along the shaft 12.

Figure 4:
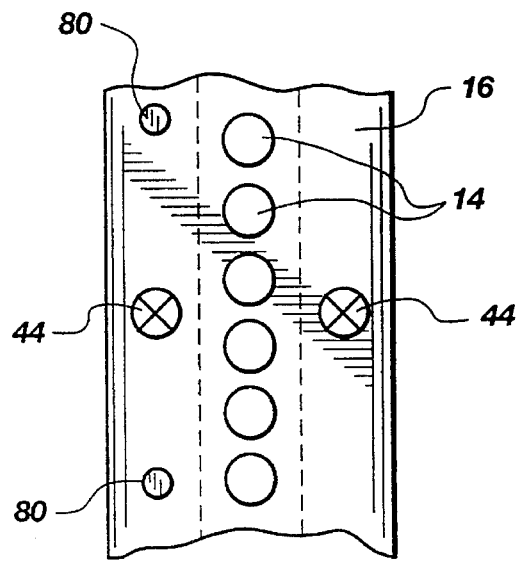
FIG. 4 is a partial end view of the guide block and bores with the shafts removed for clarity of illustration.

Referring once more to FIG. 3, the guide block 16 is secured to the sides 36 and 38 by screws 44. Seals 34 are provided between the guide block 16 and the sides 36 and 38 of the chamber 20 to reduce gas leakage. The seals may be formed of latex, rubber, silicone, or similar conventional materials. The screws 44 and their relation to the guide block 16 and the bores 14 are further illustrated in FIG. 4.

Pressurized gas is provided to the chamber 20 from an external source (22 in FIG. 1) such as a conventional compressed gas tank. A conventional pressure regulator and a conventional pressure gauge are provided on a tube (46 in FIG. 2) connecting the gas source (22 in FIG. 1) to the chamber (20 in FIG. 2). The pressure regulator and pressure gauge are used to ensure that chamber (20 in FIG. 2) is pressurized according to the teachings of the present invention.

Inert gases such as nitrogen or argon are presently preferred. However, those of skill in the art will appreciate that any gas may be used which does not react unfavorably with the guide block 16, the shafts 12, with other objects, or with persons exposed to the gas.

The gas travels under pressure through the tube 46 to a gas tube connector 48 secured to the frame 18. Conventional tubes, conduits, valves, pressure gauges, and pressure regulators may be used to carry, monitor, and regulate the flow of pressurized gas through the device 10. Within the frame 18, the gas travels through an inlet conduit 50 to a conventional three-way valve 52. The valve 52 is positionable in an inlet position, an outlet position, and a blocking position by turning a handle 53. In the inlet position, the valve 52 permits gas to flow from the inlet conduit 50 into a diffusion chamber 54. The diffusion chamber 54 is separated from the chamber 20 by a wall 56, but is in continual fluid communication with the chamber 20 via orifices 58 in the wall 56. Thus, when the valve 52 is in the inlet position, pressurized gas may flow from the external source (22 in FIG. 1) through the valve 52 and into the chamber 20.

When the valve 52 is in the outlet position and the gas pressure inside the chamber 20 exceeds the ambient atmospheric gas pressure, gas may flow out from the chamber 20, through an outlet conduit 60 and a gas outlet 62 to the atmosphere. Finally, when the valve 52 is in the blocking position, the chamber 20 is cut off from fluid communication with either the inlet conduit 50 or the outlet conduit 60.

The device 10 also includes a limiter slide, indicated generally at 64 in FIG. 2. The limiter slide 64 includes a bracket 66 and a bar 68. The bracket 66 is mounted to the frame 18 on a cervical end (102 in FIG. 1) of the frame 18 near the guide block 16. The bar 68 is configured for slidable engagement relative to the bracket 66. The bar 68 may be fixed in position by tightening a screw 70 in the bracket 66 so that the screw 70 presses against the bar 68. When the screw 70 is not tightened against the bar 68, the bar is slidable from a position in which the bar does not engage any shaft 12 to at least one position in which the bar engages the external end 26 of at least one shaft 12. By so engaging the shaft 12, the bar 68 prevents movement of the engaged shaft 12 relative to the guide block 16 beyond the bar 68.

Figure 5:
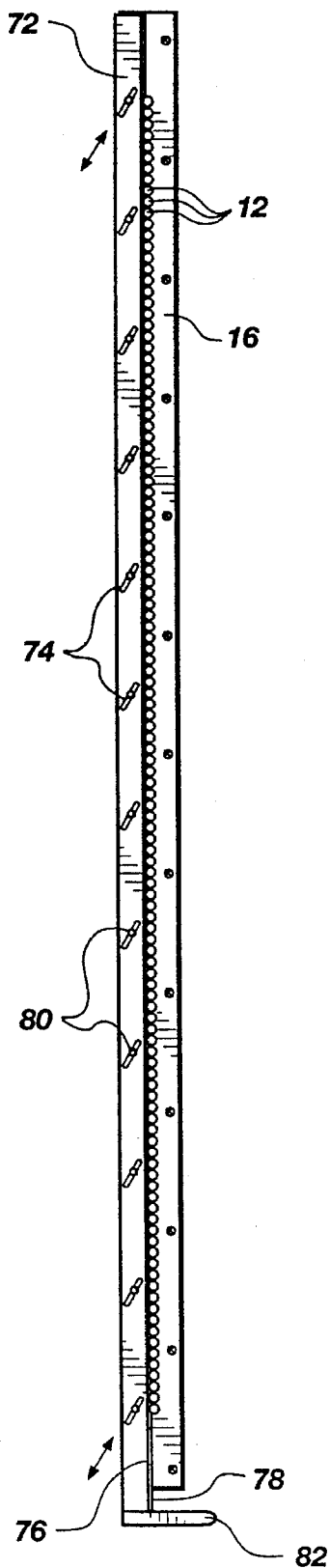
FIG. 5 is an end view of the chamber frame shown in FIG. 1, further illustrating the keeper strip.

As best illustrated in FIG. 5, the device 10 also includes a keeper strip 72 for locking the shafts 12 into position relative to the guide block 16. The keeper strip 72 includes a rigid strip of acrylic or similar material having diagonal slots 74 therein. The edge 76 of the keeper strip 72 nearest the shafts 12 carries a layer 78 of cork or latex. The keeper strip 72 is slidably mounted to the guide block 16 by pins 80 which pass through the slots 74 into the guide block 16. A handle 82 of molded plastic or other light weight rigid material is mounted to one end of the keeper strip 72.

The keeper strip 72 is movable from a released position in which it does not engage the shafts 12 to a locked position. In the locked position, the layer 78 of the keeper strip 72 presses against the shafts 12. This in turn presses each shaft 12 against an interior edge of the bore 14 through which the shaft 12 passes, thereby locking the shafts 12 in position relative to the guide block 16. The back face of the keeper strip 72, which is contiguous with the guide block 16, is covered by a layer of latex. The latex layer contains slots corresponding to the diagonal slots 74. The latex layer provides a frictional contact against the pins 80 to maintain the keeper strip in the locked position until sufficient force is applied to the handle 82 to move the keeper strip 72 back to its released position.

As shown in FIG. 1, the chamber frame 18 may be mounted on a mobile stand 84 having a positionable arm 86. The mobile stand 84 is equipped with wheels 88. The mobile stand 84 may be, for instance, a conventional X-ray stand which has been retrofitted for use in connection with the frame 18 and other elements of the device 10. The positionable arm 86 permits deployment of the shafts 12 against the backs of patients in various standing (indicated by dotted line 90), lying, flexing, extending, or other positions.

Figure 6:
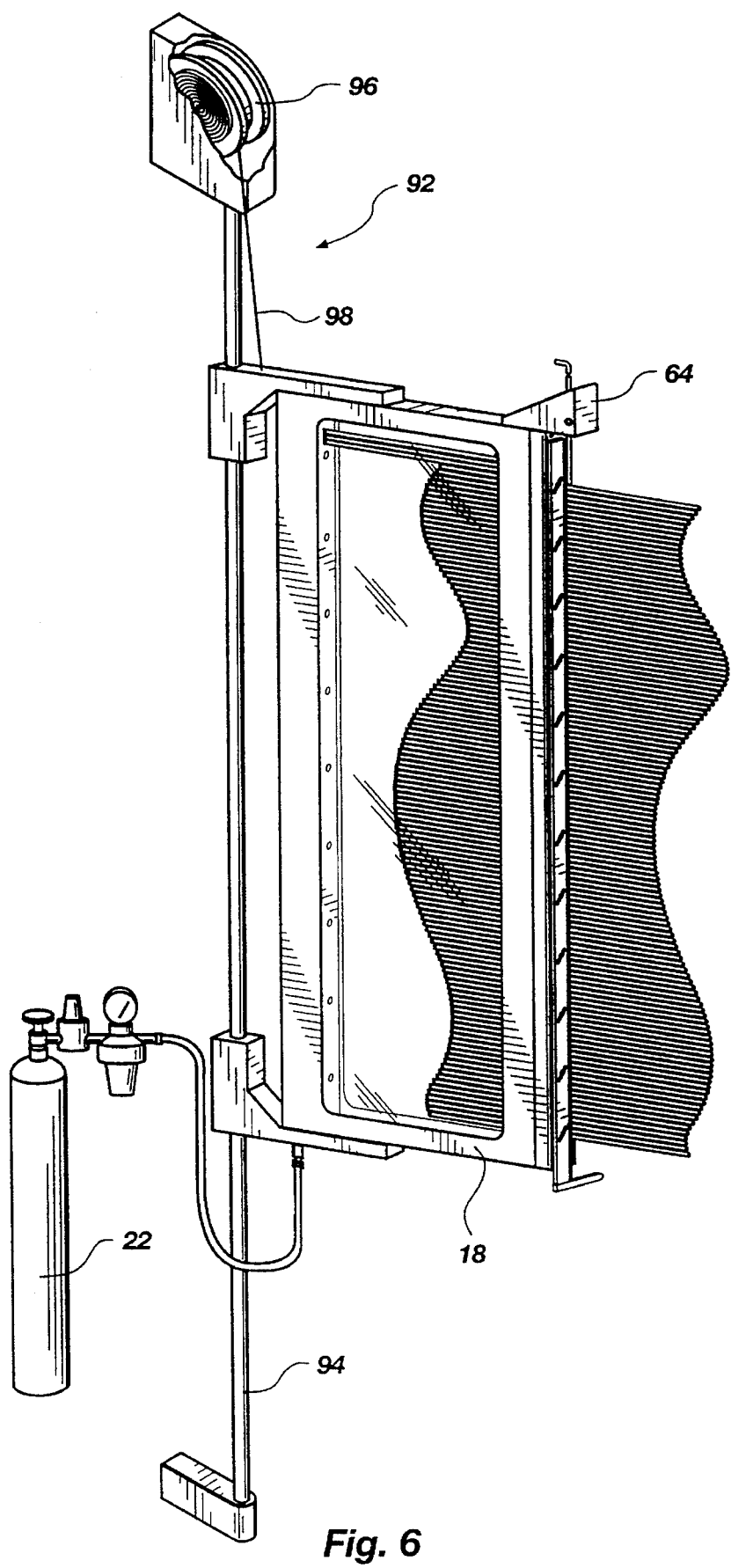
FIG. 6 is an alternative embodiment of the present invention, illustrating a stand which includes a vertical column capable of being mounted to a wall.

Alternatively, the chamber frame 18 may be mounted on a vertical wall mount, indicated generally at 92 in FIG. 6. In this case, the chamber frame 18 slides up and down along a vertical column 94 which is mounted to a wall (not shown). The frame 18 is attached to a recoil spring 96 via a cable 98 to counterbalance the frame 18. The frame 18 may thus be positioned for use on patients having a wide range of heights. The wall mount 92 requires minimal storage space, permitting the gauge 10 to be stored against the wall when not in use. In its stored position, the gauge 10 extends only about five centimeters from the wall.

In operation, a patient is first placed in a clinically useful position. For instance, the patient may be placed in a substantially vertical standing position to assess the patient's spine contours, as indicated by the broken line 90 in FIG. 1. Alternatively, the patient may be placed in a sequence of positions, with measurements taken in each position. The positionable arm 86 permits the gauge 10 to be employed to measure spinal contours of patients in all these positions, as well as patients who are lying horizontally on one side so as to present their spine.

After the patient is properly placed, the spine contour gauge 10 is positioned near the patient's spine. The gauge 10 is positioned in substantial alignment with the patient's spinal column, so that the patient's left side is on one side of the plane defined by the shafts 12 and the patient's right side is on the other side of that plane.

The gauge 10 may be placed so that the shafts 12 near a pelvic end 100 of the frame 18 will deploy on both sides of the apex of the pelvic curve and the shafts 12 near the cervical end 102 of the frame 18 will deploy against the top of the occipital bone. This enables the device 10 to fully capture the contours of the cervical, dorsal, and lumbar curves of the patient's spine. With shorter patients, the bar 68 of the limiter slide 64 may be positioned to prevent the shafts 12 at the head end 102 of the frame 18 from deploying against the patient's head above the cervical curve.

The shafts 12 are then deployed by turning the handle 53 until the valve (52 in FIG. 2) reaches the inlet position, thereby permitting pressurized gas to flow from the source 22 into the chamber 20. The increased gas pressure inside the chamber 20 gently urges the shafts 12 further out of the chamber 20 until they come to rest against the limiter slide bar 68 or the patient's spine, or until the stops (30 in FIG. 2) engage the guide block 16.

The velocity of the shafts 12 as they deploy in this manner is small, because the shafts 12 fit snugly within their bores 14 and because the gas pressures are relatively low. Moreover, the ends 26 of the shafts 12 are covered with soft tips 28. Thus, the impact of the ends 26 against the patient's tissue when the shafts 12 are deployed does not discomfort the patient. Because the gas pressure inside the chamber 20 provides a substantially uniform force against all the shafts 12, the tissue about the patient's spine is compressed uniformly, thereby providing more accurate measurements.

After the shafts 12 are deployed in this manner, the keeper strip 72 is urged into its locking position to preserve the shaft positions. The valve handle 53 is turned to an outlet position to release the pressure in the chamber 20. The patient may then move away from the gauge 10.

Referring now to FIG. 2, the medical professional obtains quantified shaft positions which correspond to the contours of the patient's spine by reading the measuring indicia 40 and the identifying indicia 42. The shaft positions may also be recorded by tracing the end points 24. For instance, the end points 24 may be traced onto a sheet of static plastic film that has been placed against the transparent chamber side 38. One acceptable film is the flexible synthetic film sold under the mark MYLAR by E. I. Du Pont de Nemours and Co. The medical professional may then show this tracing to the patient, refer to it while explaining the patient's condition, and use it to motivate the patient.

Assuming that coordinates are needed as a basis for further processing, the values read are recorded, for instance, by entry into a preprogrammed computer (104 in FIG. 1). Depending on the contour or flexibility measurement being sought, it may be necessary to read all the coordinates for all deployed shafts 12, or only to determine the coordinates of selected shafts 12. For instance, if the medical professional is only measuring the dorsal curve, coordinates from shafts 12 deployed against other curves may be omitted from consideration.

In accordance with the teachings of the present invention, these quantified shaft positions are processed, by hand or by computer, to obtain a quantitative summary that is useful to the professional and understandable by the patient. One such processing method includes computation of the ratio of a spinal contour's height to its length to yield a single numeric value representing curvature. The height is measured from the top of the selected spinal contour to a tangent line which passes through the ends of the selected spinal contour. The length is the length of the tangent line between the ends of the selected spinal contour. As a baseline, it will be appreciated that this height-to-length ratio approaches 1/2 as the curve being measured approaches a semi-circle, and approaches zero as the measured curve flattens into a straight line.

Another method for processing the quantified shaft positions includes initially calculating the radius of the curve at several predetermined locations along the curve. Each radius is measured from the predetermined location on the curve to the center of the curve. The center is the point of intersection between a tangent line and an apex-normal line. The tangent line is the line passing through the end points of the curve. The apex-normal line is a line normal to the tangent line passing through the apex of the curve. These radius values may then be averaged to obtain an average radius. Finally, an average curvature may be obtained by taking the reciprocal of the average radius.

The quantified shaft positions may also be fit to polynomials by known methods to obtain a quantitative summary consisting of several values rather than a single value as in the previous two examples. Thus, the shaft positions may be fit to a second-order polynomial such that the quantitative summary consists of the constant coefficients a, b, and c of the polynomial $a+bx+cx^2$ which best approximates the curve according to a least-squares test. Cubic splines and other algebraically tractable curves which approximate the quantified shaft positions may also be obtained by known methods.

For assisting the professional in processing the shaft positions, the device 10 illustrated in FIG. 1 includes a preprogrammed calculator 104. One acceptable calculator 104 is a dedicated Hewlett-Packard model HP 48GX which has been modified to prompt the professional for predetermined shaft positions and to process the shaft positions entered. The calculator 104 calculates second-order polynomial approximations of the cervical, dorsal, and lumbar curves of the patient's spine. The calculator 104 may also be programmed to calculate an average curvature or to provide other quantitative summaries according to the teachings of the present invention.

Quantitative summaries of a selected spinal contour may also be combined to calculate a quantitative measurement of the flexibility of the selected contour. For instance, flexibility may be defined as the difference in curvature from flexion to extension. That is, the patient is placed in a position flexing the spine, the shafts 12 are deployed, the indicia 40 and 42 are read, and a method such as those outlined above is used to process the coordinates to obtain a quantitative summary representing the curvature of a selected contour in flexion. Then the patient is placed in a position extending the spine, these steps are repeated, and a quantitative summary representing the curvature of the selected contour in extension is obtained. Finally, the difference between the two curvatures is calculated, producing a quantitative measurement of the flexibility of the selected contour.

From the foregoing, it will be appreciated that the present invention provides a gauge for reliably measuring spinal contours. Once the shafts are deployed against a selected spinal contour, the relative positions of the internal ends of the shafts accurately capture the shape of the contour. Moreover, the gauge can be operated by a medical professional with little additional training. The shafts are deployed quickly and easily by turning the valve to permit pressurization of the chamber. The resulting shaft positions are easily read from the indicia on the device, and the preprogrammed calculator minimizes the effort needed to process the quantified shaft positions.

Because low pressures are used and the chamber is not large, relatively little gas is expended each time the shafts are deployed. Thus, the spinal contour gauge is inexpensive to operate. The device may be mounted on a portable stand with a positionable arm, or mounted vertically on a wall in a manner that requires minimal storage space.

The methods of the present invention for obtaining and processing spinal measurements provides quantitative results that are useful to medical professionals and understandable by their patients. Accurate measurement of the patient's progress over time is available, because the measurements obtained are not subjective. Characteristics such as spinal flexibility which were previously not reliably quantified may also be obtained easily and accurately.

What is claimed and desired to be secured by patent is:

1. A spine contour gauge, comprising:
    a guide block having a plurality of parallel coplanar bores;
    a frame secured to the guide block, the frame and the guide block substantially defining a chamber;
    a plurality of substantially parallel coplanar shafts, each shaft having an internal end disposed within the chamber, a body disposed within a bore of the guide block for movement relative to the block, and an external end disposed outside the chamber; and
    a pressurized gas source in fluid communication with the chamber capable of pressurizing the chamber to an actuating gas pressure in the range from about five to about 100 kilopascals (about one to about 15 p.s.i.) above atmospheric pressure.

2. The device of claim 1, wherein the actuating gas pressure in the chamber is in the range from about five to about ten kilopascals (about one to about two p.s.i.).

3. The device of claim 1, wherein a portion of the guide block about each bore comprises a synthetic resin, and wherein the body of each shaft comprises aluminum.

4. The device of claim 3, wherein the synthetic resin is selected from the group consisting of acetal resin, DELRIN, and ERTALYTE.

5. The device of claim 1, wherein the frame includes a transparent side revealing the positions of the internal ends of the shafts within the chamber.

6. The device of claim 5, wherein the transparent side comprises a plastic sheet.

7. The device of claim 1, wherein the external tip of each shaft comprises a soft material to cushion impact of the external end of the shaft against human tissue.

8. The device of claim 1, further comprising:
    a gas outlet adjacent the frame for releasing pressurized gas from the chamber; and
    a three-way valve in fluid communication with the gas outlet and the pressurized gas source, the three-way valve positionable between an inlet position for permitting gas to flow from the pressurized gas source into the chamber to pressurize the chamber, an outlet position for permitting gas to flow out of the chamber through the gas outlet, and a blocking position for cutting off fluid communication between the chamber, the gas outlet, and the pressurized gas source.

9. The device of claim 1, wherein the pressurized gas source is a source of pressurized inert gas.

10. The device of claim 1, further comprising a lock for locking the plurality of shafts into a fixed position with respect to the guide block.

11. The device of claim 10, wherein the lock includes a rigid keeper strip slidably mounted to the guide block adjacent the shafts, the keeper strip movable between a released position in which the keeper strip does not engage the shafts and a locked position in which the keeper strip presses each shaft against an interior edge of the bore through which the shaft passes, thereby locking the shafts in position relative to the guide block.

12. The device of claim 1, further comprising a limiter slide including a bracket and a bar, the bracket mounted near the guide block, the bar configured for slidable engagement relative to the bracket from a position in which the bar does not engage any shaft to a position in which the bar engages the external end of at least one shaft, thereby preventing movement of the engaged shaft relative to the guide block beyond the bar.

13. A spine contour gauge, comprising:
a guide block having a plurality of parallel coplanar bores, a portion of the guide block about each bore comprising a synthetic resin;
a frame secured to the guide block and including a transparent side, the frame and the guide block substantially defining a chamber;
a plurality of substantially parallel coplanar shafts, each shaft having an internal end disposed within the chamber, a body disposed within a bore of the guide block, and an external end disposed outside the chamber, the body of each shaft comprising aluminum; and
a pressurized inert gas source in fluid communication with the chamber.

14. The device of claim 13, further including measuring indicia on one of the sides of the frame for indicating the position of the internal ends of the shafts relative to the guide block.

15. The device of claim 13, further including identifying indicia along the guide block for identifying the individual shafts.

16. The device of claim 13, wherein the plurality of shafts includes at least 90 shafts per meter of guide block length.

17. The device of claim 13, wherein the diameter of the shafts is within about five micrometers of the diameter of the bores.

18. The device of claim 17, wherein the diameter of the shafts is within about 3.5 micrometers of the diameter of the bores.

19. The device of claim 13, further comprising a stop positioned at the internal end of each shaft, the stop being sufficiently large to prevent the internal end of the shaft from passing through the bore in the guide block.

20. The device of claim 13, wherein the external tip of each shaft comprises a soft material selected from the group consisting of latex and rubber.

21. The device of claim 13, further comprising:
a gas outlet adjacent the frame for releasing pressurized inert gas from the chamber; and
a three-way valve in fluid communication with the gas outlet and the pressurized inert gas source, the three-way valve positionable between an inlet position for permitting inert gas to flow from the pressurized inert gas source into the chamber to pressurize the chamber, an outlet position for permitting inert gas to flow out of the chamber through the gas outlet, and a blocking position for cutting off fluid communication between the chamber, the gas outlet, and the pressurized inert gas source.

22. The device of claim 13, wherein the pressurized inert gas source is a source of an inert gas selected from the group consisting of nitrogen and argon.

23. The device of claim 13, further comprising a rigid keeper strip slidably mounted to the guide block adjacent the shafts, the keeper strip movable between a released position in which the keeper strip does not engage the shafts and a locked position in which the keeper strip presses each shaft against an interior edge of the bore through which the shaft passes, thereby locking the shafts in position relative to the guide block.

24. The device of claim 23, wherein the keeper strip has a plurality of angled slots and is mounted to the guide block on pins which protrude from the guide block and engage the angled slots.

25. The device of claim 13, wherein the frame has a cervical end and a pelvic end, further comprising a limiter slide including a bracket and a bar, the bracket mounted near the cervical end of the frame, the bar configured for slidable engagement relative to the bracket from a position in which the bar does not engage any shaft to at least one position in which the bar engages the external end of at least one shaft, thereby preventing movement of the engaged shaft relative to the guide block beyond the bar.

26. The device of claim 25, wherein the limiter slide bar is capable of extending a sufficient distance toward the pelvic end of the frame to engage shafts along at least about 20 centimeters of the length of the bar.

27. The device of claim 13, further comprising a computer programmed to accept input values corresponding to the positions of a plurality of shafts relative to the guide block, and to process the inputs to produce a quantitative summary of the input values.

28. The device of claim 13, further comprising a stand to which the frame is adjustably secured.

29. The device of claim 28, wherein the stand is mounted on wheels, the stand comprising an arm secured to the frame, the arm capable of supporting the frame in vertical, horizontal, and tilted orientations.

30. The device of claim 28, wherein the stand comprises a vertical column secured to a wall and a recoil spring connected to the frame by a cable, the recoil spring capable of counterbalancing the weight of the frame, the guide block, and the shafts.

31. A method for quantitatively summarizing selected contours of a patient's spine, comprising the steps of:
positioning a spine contour gauge near the patient's spine, the spine contour gauge comprising a plurality of substantially parallel coplanar shafts mounted in a guide block for movement from a retracted position to a deployed position in which one end of the shafts contact the patient along the patient's spine, the spine contour gauge further comprising positioning indicia for quantifying the position of each shaft relative to the other shafts;
deploying the shafts such that one end of each shaft contacts the patient along the patient's spine;
reading the positioning indicia of a predetermined set of shafts to obtain quantified shaft positions; and
processing the quantified shaft positions to obtain a quantitative summary of a selected contour of the patient's spine, said processing step comprising at least one step selected from the group consisting of:
computing curvature for a selected spinal contour by calculating the reciprocal of the average radius of the curve defined by the selected spinal contour;
computing the ratio of a height to a length for a selected spinal contour, wherein the height is measured from the apex of the selected spinal contour to a tangent line passing through the ends of the selected spinal contour, and wherein the length is the distance along the tangent line between the ends of the selected spinal contour; and fitting the quantified shaft positions to a polynomial curve.

32. The method of claim 31, wherein the step of positioning the spine contour gauge is preceded by the step of placing the patient in a horizontal lying position.

33. The method of claim 31, wherein the positioning step is preceded by the step of placing the spine of the patient in flexion and the quantitative summary is a first quantitative summary of the spinal contour in flexion, and further comprising the steps of:

placing the spine of the patient in extension;

repeating the steps of positioning the spine contour gauge, deploying the shafts, reading the positioning indicia, and processing the quantified shaft positions, thereby obtaining a second quantitative summary which is a quantitative summary of the spinal contour in extension; and calculating a quantitative measurement of the flexibility of the selected contour based on the quantitative summaries of the contour in flexion and the contour in extension.

34. The method of claim 31, wherein the deploying step comprises pressurizing a chamber with a pressurized gas, the chamber substantially defined by the shafts, the guide block, and a frame, wherein one end of each shaft is positioned within the chamber, thereby urging the shafts to deploy.

35. The method of claim 31, further comprising the step of tracing the end points of the shafts.

36. The method of claim 35, wherein said tracing step comprises tracing the end points of the shafts onto a sheet of static plastic film.

* * * * *